United States Patent
Shainwald et al.

(10) Patent No.: US 11,832,788 B2
(45) Date of Patent: Dec. 5, 2023

(54) SURGICAL INSTRUMENTS WITH ROTATION STOP DEVICES AND RELATED METHODS

(71) Applicant: MEDOS INTERNATIONAL SÀRL, Le Locle (CH)

(72) Inventors: Mark Shainwald, Bridgewater, MA (US); Jacob A. Marks, Mansfield, MA (US)

(73) Assignee: Medos International Sarl, Le Locle (CH)

( * ) Notice: Subject to any disclaimer, the term of this patent is extended or adjusted under 35 U.S.C. 154(b) by 0 days.

(21) Appl. No.: 17/695,407

(22) Filed: Mar. 15, 2022

(65) Prior Publication Data

US 2022/0206524 A1   Jun. 30, 2022

Related U.S. Application Data

(62) Division of application No. 15/946,016, filed on Apr. 5, 2018, now Pat. No. 11,294,414.

(51) Int. Cl.
| A61B 17/28 | (2006.01) |
|---|---|
| A61B 17/34 | (2006.01) |
| F16M 11/08 | (2006.01) |
| A61B 1/05 | (2006.01) |

(Continued)

(52) U.S. Cl.
CPC ...... *A61B 1/00066* (2013.01); *A61B 1/00105* (2013.01); *A61B 1/00112* (2013.01); *A61B 1/00147* (2013.01); *A61B 1/05* (2013.01); *A61B 17/2841* (2013.01); *A61B 17/3417* (2013.01); *F16M 11/08* (2013.01); *G05G 5/04* (2013.01); *F16M 2200/021* (2013.01)

(58) Field of Classification Search
CPC ... A61B 1/00066; A61B 1/00105; A61B 1/05; A61B 17/2841; A61B 17/3417; A61B 2017/0046; F16M 11/08; F16M 2200/021; G05G 1/08; G05G 5/04
See application file for complete search history.

(56) References Cited

U.S. PATENT DOCUMENTS

| 2,620,911 A | 12/1952 | Krell |
|---|---|---|
| 2,631,709 A | 3/1953 | Anderson |
| 3,015,793 A | 1/1962 | Fraser et al. |

(Continued)

FOREIGN PATENT DOCUMENTS

| EP | 0165727 A1 | 12/1985 |
|---|---|---|
| JP | H06269406 A | 9/1994 |

(Continued)

OTHER PUBLICATIONS

Partial Extended European Search Report for Application No. 19167273.2, dated Sep. 5, 2019 (12 pages).

(Continued)

*Primary Examiner* — Anh Tuan T Nguyen
*Assistant Examiner* — Shankar Raj Ghimire

(57) ABSTRACT

Surgical instruments with rotation stop devices and related methods are disclosed herein, e.g., for providing limited rotation between first and second components of the surgical instrument in a range greater than 360 degrees. Exemplary rotation stop devices can have a low profile and can include various features to facilitate packaging of the device within a larger instrument.

8 Claims, 5 Drawing Sheets

(51) Int. Cl.
*A61B 1/00* (2006.01)
*G05G 5/04* (2006.01)

(56) References Cited

U.S. PATENT DOCUMENTS

| | | | |
|---|---|---|---|
| 3,037,397 | A | 6/1962 | Allen et al. |
| 3,069,914 | A | 12/1962 | Laubenfels |
| 3,203,262 | A | 8/1965 | Beer |
| 3,262,535 | A | 7/1966 | De Pasqua |
| 3,293,925 | A | 12/1966 | Linsley |
| 3,762,227 | A | 10/1973 | Bohnhoff |
| 4,064,981 | A | 12/1977 | House et al. |
| 4,760,907 | A | 8/1988 | Avny |
| 5,185,004 | A | 2/1993 | Lashinski |
| 5,255,882 | A | 10/1993 | Schroppel |
| 5,383,876 | A | 1/1995 | Nardella |
| 5,479,929 | A | 1/1996 | Cooper et al. |
| 5,673,593 | A | 10/1997 | Lafferty |
| 5,784,435 | A | 7/1998 | Figurski |
| 6,113,556 | A | 9/2000 | Avitall |
| 8,808,284 | B2 | 8/2014 | Pellegrino et al. |
| 9,155,565 | B2 | 10/2015 | Boomer et al. |
| 9,561,045 | B2 | 2/2017 | Hinman et al. |
| 9,775,627 | B2 | 10/2017 | Patel et al. |
| 10,357,269 | B2 | 7/2019 | Worrell et al. |
| 10,446,058 | B2 | 10/2019 | Collins, Jr. |
| 10,588,691 | B2 | 3/2020 | Pellegrino et al. |
| 10,610,269 | B2 | 4/2020 | Mickiewicz et al. |
| 11,294,414 | B2 | 4/2022 | Shainwald et al. |
| 2005/0182409 | A1 | 8/2005 | Callahan et al. |
| 2009/0087252 | A1 | 4/2009 | Kolster |
| 2010/0249497 | A1 | 9/2010 | Peine et al. |
| 2011/0144576 | A1* | 6/2011 | Rothe .................. A61B 1/0052 604/95.04 |
| 2012/0238819 | A1 | 9/2012 | Long et al. |
| 2016/0327200 | A1 | 11/2016 | Crooks |
| 2017/0172386 | A1 | 6/2017 | Okamoto |
| 2017/0188795 | A1* | 7/2017 | Ouyang ................ A61B 1/018 |
| 2017/0231474 | A1 | 8/2017 | Saadat et al. |
| 2017/0325671 | A1 | 11/2017 | Hopkins, Jr. |
| 2018/0161047 | A1 | 6/2018 | Purdy et al. |
| 2019/0125320 | A1* | 5/2019 | Shelton, IV ............ F16D 11/16 |
| 2019/0208143 | A1* | 7/2019 | Brooks .................... A61B 1/05 |
| 2019/0310681 | A1 | 10/2019 | Shainwald et al. |
| 2020/0205722 | A1 | 7/2020 | Sarna |

FOREIGN PATENT DOCUMENTS

| | | |
|---|---|---|
| JP | H07504834 A | 6/1995 |
| JP | 2013006038 A | 1/2013 |
| JP | 2016512971 A | 5/2016 |
| JP | 2018047264 A | 3/2018 |
| WO | 2017040692 A1 | 3/2017 |
| WO | 2017095770 A1 | 6/2017 |

OTHER PUBLICATIONS

Extended European Search Report for Application No. 21197668.3, dated Dec. 7, 2021 (8 pages).
First Examination Report for Indian Application No. 201914012043, dated Jul. 18, 2022 (7 pages).
Japanese Office Action for Application No. JP 2019-066538, dated Mar. 8, 2023 (19 pages).

* cited by examiner

SURGICAL INSTRUMENTS WITH ROTATION STOP DEVICES AND RELATED METHODS

CROSS-REFERENCE TO RELATED APPLICATIONS

This application claims the benefit of and is a division of U.S. patent application Ser. No. 15/946,016, filed Apr. 5, 2018, which is hereby incorporated by reference in its entirety.

FIELD

Surgical instruments with rotation stop devices and related methods are disclosed herein, e.g., for providing limited rotation between first and second components of the surgical instrument in a range greater than 360 degrees.

BACKGROUND

There are many instances in which it may be desirable to limit the degree to which first and second components can rotate relative to one another. For example, in a surgical instrument having a knob rotatable relative to a handle to manipulate a distal end of the surgical instrument, it may be desirable to limit the degree to which the knob can rotate relative to the handle. A rotation limit may be desired to avoid breaking or stressing wires, optical fibers, or other components that are twisted or bent during rotation. Existing approaches to limiting rotation generally involve fixed mechanical stops disposed at discrete angular positions about the rotation axis, providing a limited rotation range of less than 360 degrees. In some applications, limited rotation between first and second components in a range greater than 360 degrees may be desired. Existing approaches to limiting rotation may also be relatively large and difficult to package within an instrument or device.

There is a need for improved rotation stop devices and related methods.

SUMMARY

Surgical instruments with rotation stop devices and related methods are disclosed herein, e.g., for providing limited rotation between first and second components of the surgical instrument in a range greater than 360 degrees. Exemplary rotation stop devices can have a low profile and can include various features to facilitate packaging of the device within a larger instrument.

In some embodiments, a surgical instrument can include a proximal handle; a shaft extending from the handle and having a distally-mounted visualization device; a knob configured to rotate relative to the handle about a rotation axis to move the visualization device; and a rotation stop that limits rotation of the knob relative to the handle to a range greater than 360 degrees.

The instrument can include a sensor configured to detect a rotational position of the knob and to correct an electronic display of images captured by the visualization device based on the detected position. The rotation stop can include a threaded shaft mated to a threaded nut, the threaded shaft being configured to rotate with the knob and the nut being non-rotatably captured by the handle. The instrument can include a potentiometer having a shaft coupled to or formed integrally with the threaded shaft. The rotation stop device can include a threaded shaft configured to rotate with the knob and a nut having an opening in which the threaded shaft is received, the nut being non-rotatably coupled to the handle. The nut can travel along the threaded shaft between first and second rotation limits to limit rotation of the knob relative to the handle about the rotation axis. The first rotation limit can be a surface of the knob that faces the handle. The second rotation limit can be a surface of the handle that faces the knob. The distance between the first and second rotation limits can remain constant as the knob is rotated relative to the handle. The distance between the first and second rotation limits can be less than or equal to 10 mm. The instrument can include a throughhole that extends through the knob and the threaded shaft. The nut and the threaded shaft can be received within a cavity of the handle. The instrument can include an elongate member that crosses a rotation plane defined between the knob and the handle, the elongate member having a first end fixed to a portion of the instrument distal to the rotation plane and a second end fixed to a portion of the instrument proximal to the rotation plane. The elongate member can include an optical fiber, the first end of the elongate member can be coupled to a light source proximal to the rotation plane, and the second end of the elongate member can be configured to direct light into a surgical field adjacent the visualization device. The elongate member can include an electrical conductor, the first end of the elongate member can be coupled to a controller disposed proximal to the rotation plane, and the second end of the elongate member can be coupled to the visualization device. The elongate member can extend through a throughhole of the rotation stop. The throughhole can be formed in a threaded shaft of the rotation stop.

In some embodiments, a rotation stop device can include a first component; a second component, the second component being configured to rotate relative to the first component about a rotation axis; a shaft extending from the first component along the rotation axis; and a nut having an opening in which the shaft is received, the nut being non-rotatably coupled to the second component; wherein the nut travels along the shaft between first and second rotation limits to limit rotation of the first component relative to the second component about the rotation axis.

The first and second rotation limits can limit rotation of the first component relative to the second component about the rotation axis to a range greater than 360 degrees. The first rotation limit can be a surface of the first component that faces the second component. The second rotation limit can be a surface of the second component that faces the first component. The distance between the first and second rotation limits can remain constant as the first component is rotated relative to the second component. The distance between the first and second rotation limits can be less than or equal to 10 mm. The device can include a throughhole that extends through the first component and the shaft. The throughhole can extend through the second component. The first component can be retained to the second component by one or more spring tabs that extend from the second component and through the throughhole. The device can include a potentiometer having a shaft received within the throughhole. The nut and the shaft can be received within a cavity of the second component. The nut can include an inner thread mated to an outer thread of the shaft. The nut can include a pin that rides within a helical groove of the shaft. The device can include a sensor that detects a relative rotational position of the first and second components. The sensor can be at least one of a potentiometer, a Hall effect sensor, and an optical encoder.

In some embodiments, a surgical method can include inserting an instrument having a camera at a distal end thereof into a patient; rotating a first portion of the instrument relative to a second portion of the instrument to adjust a position of the camera, wherein said rotation is limited to a range greater than 360 degrees by a rotation stop; detecting a rotational position of the first portion relative to the second portion; and adjusting an electronic display of images captured by the camera based on the detected rotational position.

The first portion can include a knob and the second portion can include a handle, the knob being rotatable relative to the handle to rotate the camera relative to the handle.

DETAILED DESCRIPTION

Figure 1:
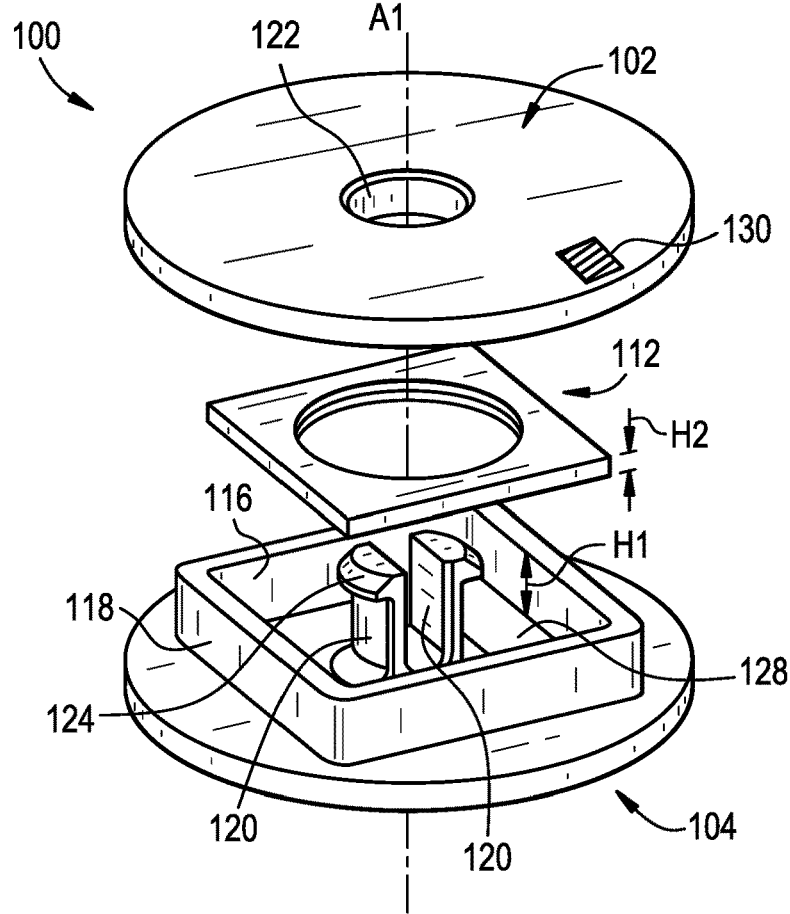
FIG. 1 is an exploded perspective view of a rotation stop device.
Figure 2:
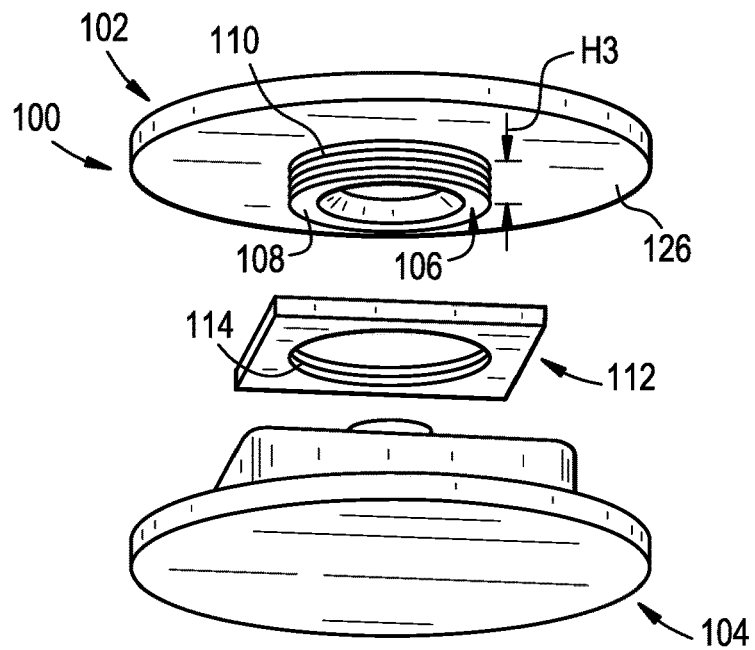
FIG. 2 is another exploded perspective view of the device of FIG. 1.
Figure 3:
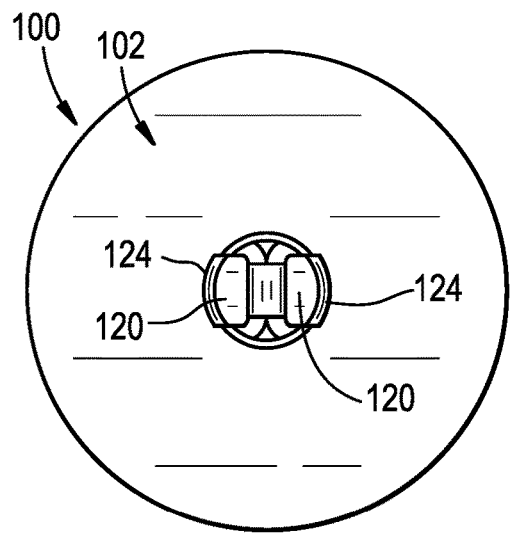
FIG. 3 is a top view of the device of FIG. 1.
Figure 4:
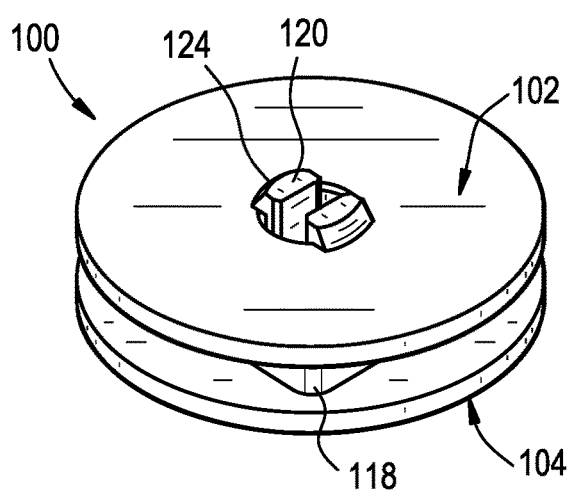
FIG. 4 is a perspective view of the device of FIG. 1.
Figure 5:
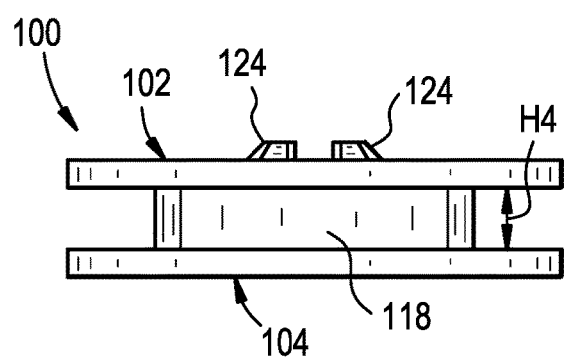
FIG. 5 is a side view of the device of FIG. 1.
Figure 6:
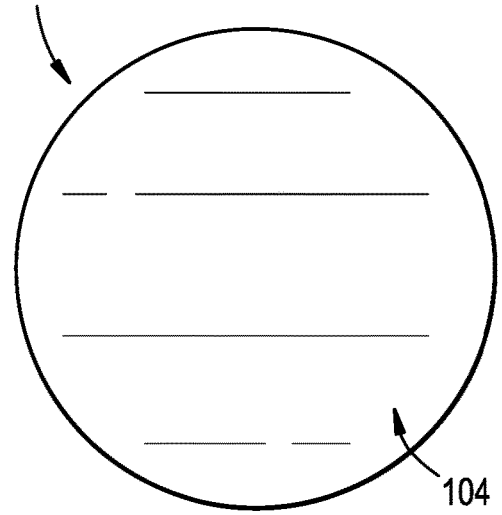
FIG. 6 is a bottom view of the device of FIG. 1.
Figure 7:
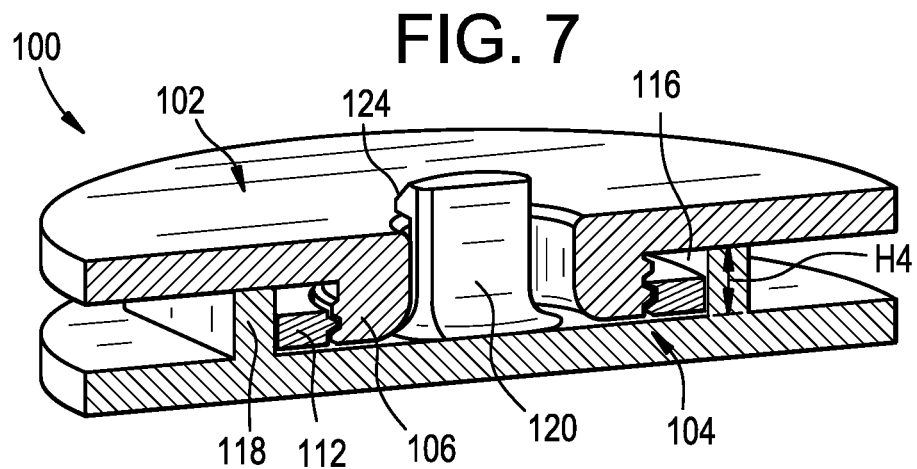
FIG. 7 is a sectional perspective view of the device of FIG. 1.
Figure 8:
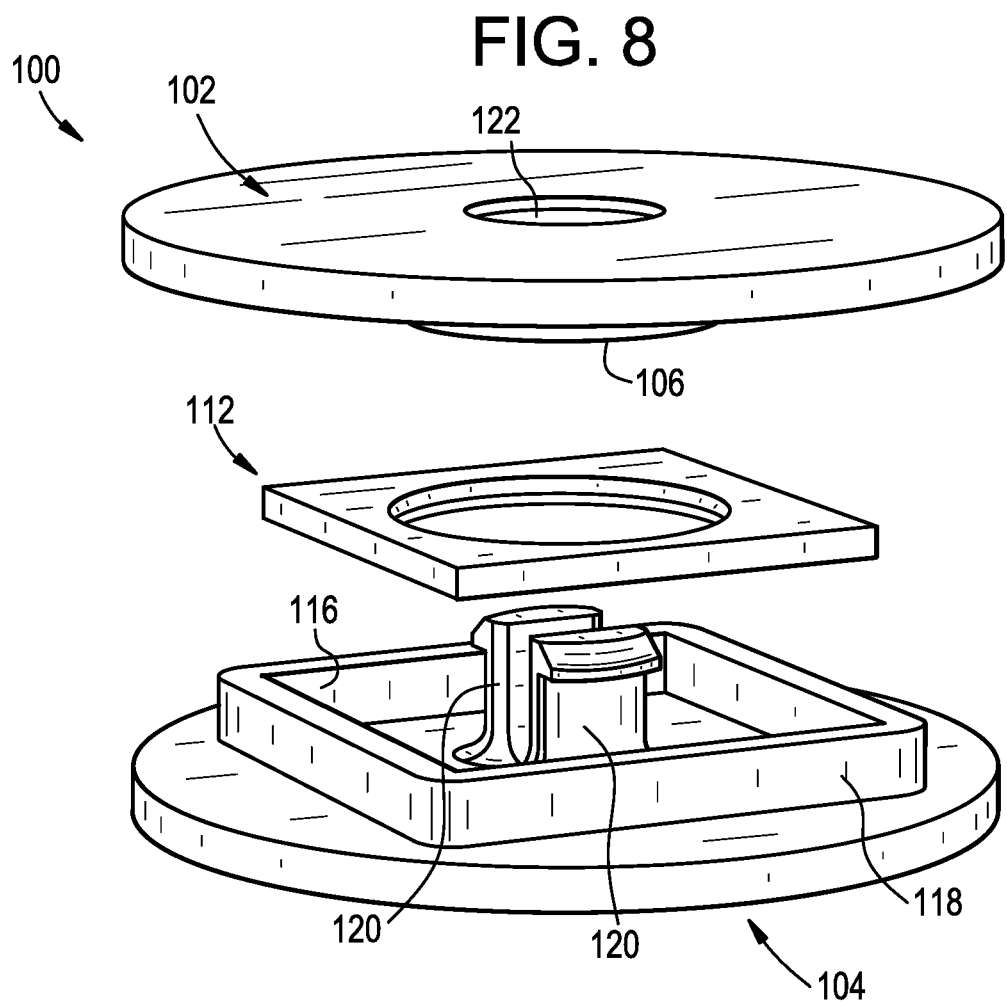
FIG. 8 is an exploded perspective view of the device of FIG. 1.

Surgical instruments with rotation stop devices and related methods are disclosed herein, e.g., for providing limited rotation between first and second components of the surgical instrument in a range greater than 360 degrees. Exemplary devices can have a low profile and can include various features to facilitate packaging of the device within a larger instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

FIGS. 1-8 illustrate an exemplary rotation stop device 100. The device 100 can allow a first component 102 to rotate relative to a second component 104 about a rotation axis A1. The device 100 can be configured to limit the degree to which the first component 102 is allowed to rotate relative to the second component 104 about the axis A1. The first component 102 can be free to rotate relative to the second component 104 up to a predetermined limit. The limit can be greater than 360 degrees. The limit can be in the range of about 0 degrees to about 720 degrees. The limit can be in the range of about 360 degrees to about 720 degrees. The limit can be in the range of about 420 degrees to about 500 degrees. The limit can be greater than 720 degrees. The limit can be less than or equal to 360 degrees. As discussed further below, the rotation stop device 100 can be incorporated into a surgical instrument, such as an endoscope, arthroscope, surgical camera, or the like, to limit rotation between components of the surgical instrument.

The first component 102 can include a threaded shaft 106. The threaded shaft 106 can extend along the rotation axis A1 between a free end 108 and a supported end 110. A nut 112 can be mated to the shaft 106. For example, the nut 112 can include an internally threaded opening 114 that is threaded onto the exterior thread of the shaft 106. While a threaded engagement is shown, it will be appreciated that the nut 112 can be mated to the shaft 106 in other ways. For example, the nut can include a pin that projects into the opening of the nut. The pin can be received within a helical groove in the exterior surface of the shaft to mate the nut to the shaft.

The second component 104 can include features for preventing rotation of the nut 112 relative to the second component 104 about the axis A1, while allowing the nut to translate relative to the second component along the axis A1. For example, the second component 104 can include a cavity 116 configured to receive the nut 112 therein. The cavity 116 can be defined by a sidewall 118. At least a portion of the sidewall 118 and at least a portion of the nut 112 can be planar or non-cylindrical and can be configured to bear against one another to prevent relative rotation between the nut and the second component 104. The cavity 116 can have a height H1 that is greater than a height H2 of the nut 112, such that the nut is capable of traveling within the cavity along the axis A1. The threaded shaft 106 can have a height H3 that substantially matches or is slightly less than the height H1 of the cavity 116. The threaded shaft 106 can have a height H3 that is greater than the height H2 of the nut 112.

While a cavity 116 is shown, it will be appreciated that other features for preventing rotation of the nut 112 relative to the second component 104 about the axis A1, while allowing the nut to translate relative to the second component along the axis A1, can be used instead or in addition. For example, the second component 104 can include a pin protruding therefrom that is laterally offset from the rotation axis A1. The pin can be slidably received within a hole formed in the nut 112. As another example, the second component 104 can include one or more planar walls that contact corresponding planar outer surface portions of the nut 112.

The device 100 can include features for retaining the first component 102 to the second component 104, while allowing rotation therebetween. For example, the second component 104 can include one or more spring tabs 120 projecting therefrom. The spring tabs 120 can be configured to snap-fit into a throughhole 122 formed in the first component 102. Each spring tab 120 can include a detent 124 that engages a groove or surface of the first component 102 to resist or prevent separation of the first component from the second component 104, while allowing the first component to rotate relative to the second component. When mated, the first component 102 can contact the upper surface of the sidewall 118 of the cavity 116, thereby forming an enclosed space in which the nut 112 is non-rotatably captured. The first component 102 and the second component 104 can be configured to remain at a fixed distance from one another along the axis A1 as the first and second components are rotated through a range of permitted rotation. While spring tabs 120 are shown, it will be appreciated that various other retention features can be used instead or in addition. In some embodiments, retention features can be omitted and features of an instrument or system in which the device 100 is packaged can be relied upon to maintain the first and second components 102, 104 at a fixed distance along the axis A1.

The device 100 can be assembled by threading the nut 112 onto the shaft 106 of the first component 102 and then inserting the shaft and the nut into the cavity 116 of the second component 104. During assembly, the spring tabs 120 of the second component 104 can pass through the throughhole 122 in the first component 102 and snap into place to lock the components together.

In use, the nut 112 can interact with the first and second components 102, 104 to limit relative rotation therebetween about the axis A1. As the first component 102 is rotated relative to the second component 104 in a first direction about the axis A1, the shaft 106 can be advanced downwards within the nut 112, causing the nut to travel upwards within the cavity 116. Rotation can continue until the nut 112 contacts an upper stop, e.g., the underside 126 of the first component 102. Since the nut 112 is constrained from rotation relative to the second component 104, further relative rotation between the first and second components in the first direction is prevented, thereby forming a first rotation limit. As the first component 102 is rotated relative to the second component 104 in a second, opposite direction about the axis A1, the shaft 106 can be retracted upwards within the nut 112, causing the nut to travel downwards within the cavity 116. Rotation can continue until the nut 112 contacts a lower stop, e.g., the upper side 128 of the second component 104 or a floor of the cavity 116. Since the nut 112 is constrained from rotation relative to the second component 104 and the second component is retained to the first component 102, further relative rotation between the first and second components in the second direction is prevented, thereby forming a second rotation limit. It will thus be appreciated that the device 100 can limit relative rotation of the first and second components 102, 104 about the axis A1 to a range defined by the first and second rotation limits. The geometries of the various components of the device 100 can be selected to achieve a desired range of permitted rotation. For example, the height H2 of the nut 112 can be increased to reduce the range of permitted rotation or can be decreased to extend the range of permitted rotation. As another example, the height H3 of the shaft 106 can be increased to increase the range of permitted rotation or can be decreased to reduce the range of permitted rotation. Other parameters can be adjusted instead or in addition, including the height of the sidewall 118, the pitch and/or lead of the threads on the shaft 106 and the nut 112, and so forth.

The device 100 can include a sensor 130 for detecting the degree of rotation between the first and second components 102, 104. The sensor 130 output can be received by a controller, processor, or circuit and used to control a system or instrument of which the device 100 is a component part. For example, the detected degree of rotation of a surgical instrument can be used to inform a surgical navigation system or surgical robot as to the position or orientation of the instrument. As another example, the detected degree of rotation of a visualization or camera instrument can be used to adjust the display of images captured by the camera, e.g., by rotating or otherwise correcting the displayed image on a screen in accordance with the rotation detected by the sensor 130. Exemplary sensors 130 can include potentiometers, Hall effect sensors, optical encoders, and the like.

The device 100 can include a throughhole 122 formed therein. The throughhole 122 can extend completely through the device 100, e.g., through the first component 102, through the shaft 106, through the nut 112, and through the second component 104, or can extend only partially through the device. The throughhole 122 can be coaxial with the rotation axis A1, can be offset therefrom, or can be obliquely angled relative thereto. The throughhole 122 can receive the spring tabs 120 discussed above to mate the first component 102 to the second component 104. Alternatively, or in addition, the throughhole 122 can receive at least a portion of another component of a system or instrument of which the device 100 is a component part. For example, the throughhole 122 can receive a knob or shaft of a potentiometer therein. This can allow the potentiometer to be positioned closer to the device 100 than would otherwise be possible, providing a reduced footprint and more efficient packaging of the device 100 within a larger system or instrument. The throughhole 122 can also be used to allow connections between parts, to route wires or optical fibers, and so forth.

The device 100 can have a low-profile, which can facilitate packaging of the device within a larger instrument or system. The distance H4 between stop surfaces 126, 128 of the device 100 can be made as small as possible. For example, the distance H4 can be less than about 20 mm, less than about 10 mm, less than about 9 mm, less than about 7 mm, and/or less than about 5 mm.

Figure 9A:
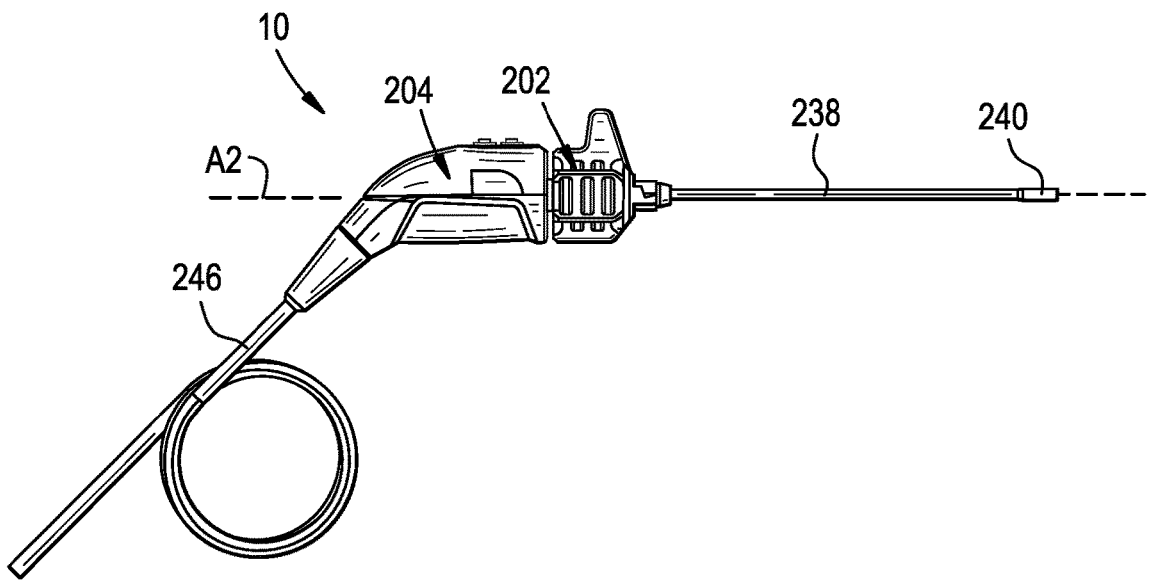
FIG. 9A is a side view of a surgical instrument that includes a rotation stop device.
Figure 9B:
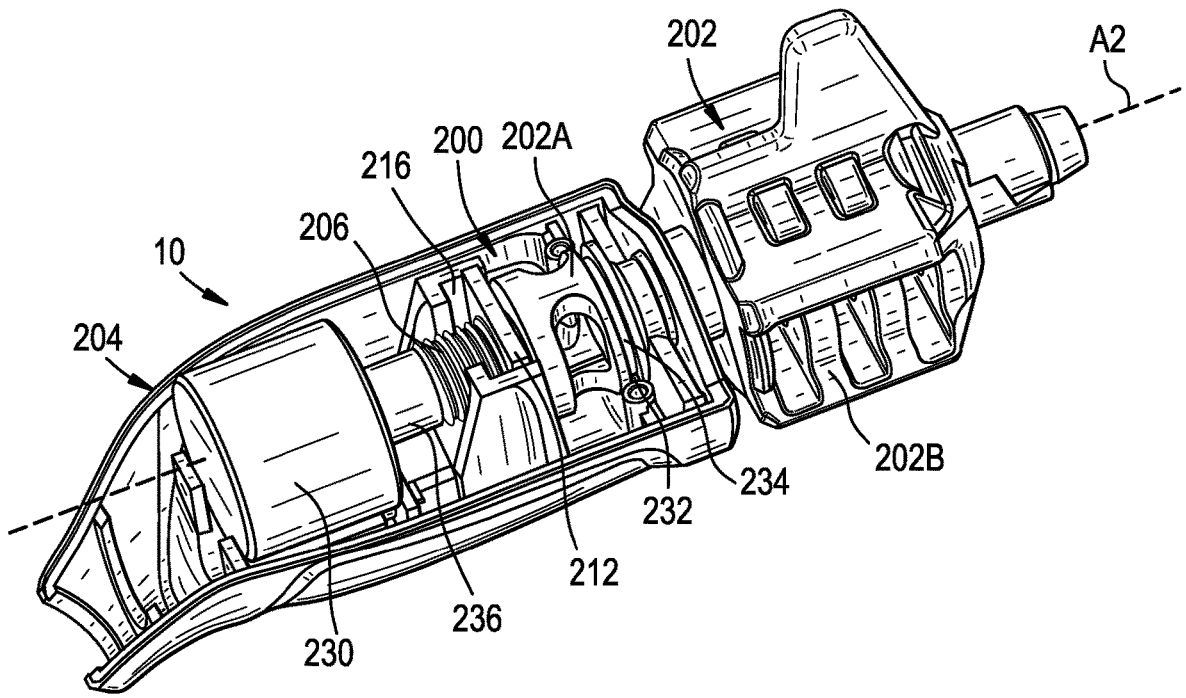
FIG. 9B is a perspective view of the instrument of FIG. 9A, shown with a handle cover removed for clarity.
Figure 9C:
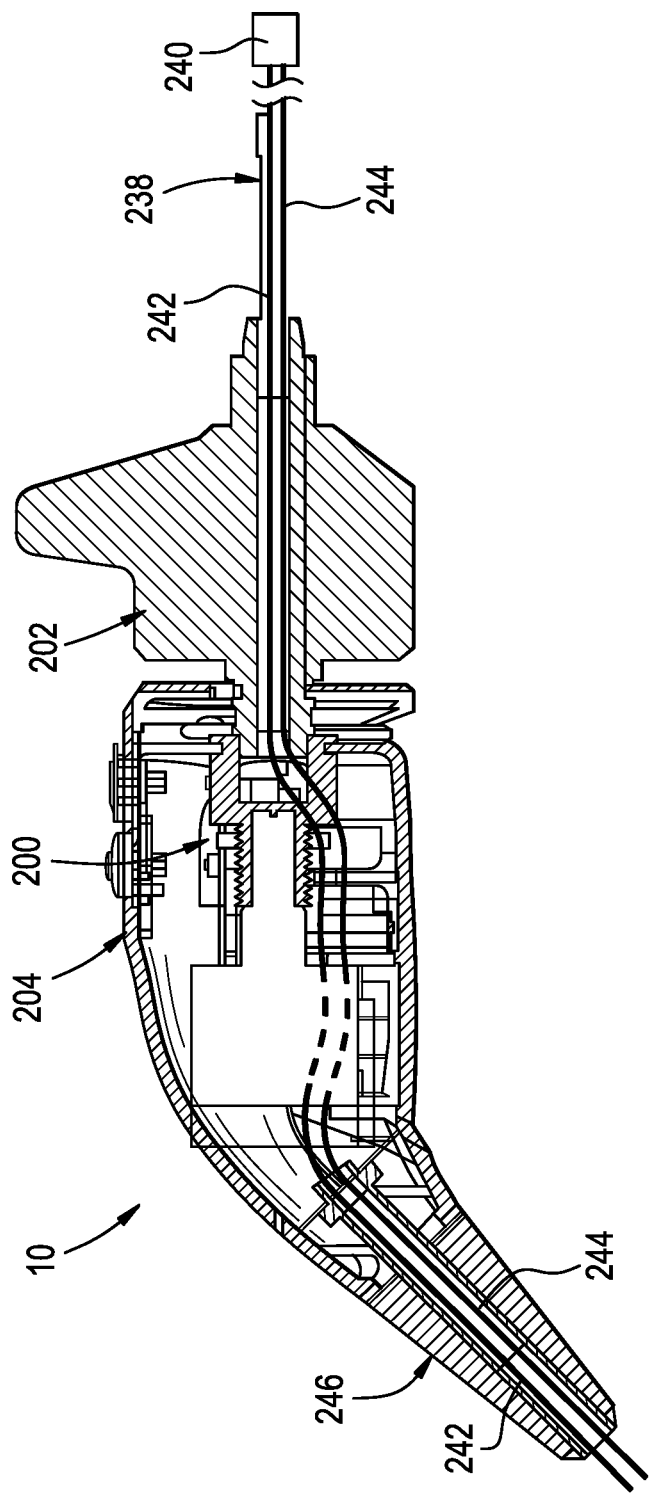
FIG. 9C is a sectional side view of the instrument of FIG. 9A.

FIGS. 9A-9C illustrate an exemplary instrument 10 that includes a rotation stop device 200 of the type described herein. The device 200 can include any of the features of the device 100 described above. The instrument 10 can be a surgical instrument, such as a surgical camera system, optical system, endoscope, arthroscope, or the like. The instrument 10 can include a proximal handle 204, which can include a housing, and a forward knob 202. The knob 202 can be rotatable relative to the handle 204 about an axis A2. Rotation of the knob 202 relative to the handle 204 about the axis A2 can be effective to rotate a distal shaft 238 of the instrument, e.g., to reposition a camera or end effector 240 within a surgical site. The rotation stop device 200 can be configured to limit rotation between the knob 202 and the handle 204. In particular, the knob 202 can serve as the "first component" of the device 200, including a threaded shaft 206 that extends along the axis A2. The knob 202 can be a monolithic component including the shaft 206 or, as shown, the shaft can be a separate component 202A attached to the main portion 202B of the knob 202. The handle 204 can serve as the "second component" of the device 200, including a cavity 216 in which a nut 212 is captured such that the nut can translate along the axis A2 but is constrained from rotating relative to the housing about the axis A2. The handle 204 and the knob 202 can be maintained at a fixed distance relative to one another along the axis A2, for example by engagement between a journal or protrusion 232 of the housing and a groove 234 of the knob. The shaft 206 can be threaded into the constrained nut 212 to allow the device 200 to limit rotation as described above.

The shaft 206 can be coupled to or formed integrally with the shaft 236 of a potentiometer 230. Accordingly, rotation of the knob 202 and, by extension, the shaft 206, can be effective to rotate the potentiometer shaft 236 to change an electric potential across the potentiometer 230. The electric potential, or changes thereto, can be sensed to determine the degree of rotation of the knob 202 relative to the handle 204. In the case of a camera instrument, the sensed degree of rotation can be used to rotate or otherwise correct an electronic display of images captured by the camera system by an amount equal to, proportional to, commensurate with, or otherwise based on the sensed degree of rotation. The rotation stop device 200 can be effective to limit rotation of the potentiometer shaft 236 at an angle greater than 360 degrees.

As shown in FIG. 9C, the instrument 10 can include one or more elongate members that cross a rotation plane defined between the knob 202 and the handle 204. A first end of the elongate member can be fixed to a portion of the instrument distal to the rotation plane and a second end of the elongate member can be fixed to a portion of the instrument proximal to the rotation plane. For example, the instrument 10 can include one or more optical fibers 242 and/or one or more electrical conductors or wires 244 that extend from a location proximal to the rotation plane (e.g., a proximal cable 246 of the instrument), across the rotation plane, and into a location distal to the rotation plane (e.g., a distal shaft 238 or camera assembly 240 of the instrument). In some embodiments, the instrument 10 can include an optical fiber 242 that directs light from a light source proximal to the handle 204 to a location adjacent a distal end of the shaft 238. In some embodiments, the instrument 10 can include an electrical conductor 244 that communicates digital or analog signals encoding image data captured by an image sensor disposed at or near the distal end of the shaft 238 from the image sensor to a controller or processor proximal to the handle 204. It will be appreciated that the rotation stop device 200 can allow the knob 202 to rotate relative to the handle 204 while limiting the rotation to an amount less than that which could damage, break, or stress the fibers 242 or conductors 244.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein can be constructed from any of a variety of known materials. Exemplary materials include those which are suitable for use in surgical applications, including metals such as stainless steel, titanium, nickel, cobalt-chromium, or alloys and combinations thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context of surgery on a human patient, it will be appreciated that the methods and devices disclosed herein can be used in any type of surgery on a human or animal subject, in non-surgical applications, on non-living objects, and so forth.

Although specific embodiments are described above, it should be understood that numerous changes may be made within the spirit and scope of the concepts described.

The invention claimed is:

1. A surgical method, comprising:
    inserting an instrument having a camera at a distal end thereof into a patient;
    rotating a first portion of the instrument relative to a second portion of the instrument about a rotation axis to adjust a position of the camera, wherein said rotation is limited to a range greater than 360 degrees by a rotation stop having a retention feature that maintains an axial position of a first component of the rotation stop relative to a second component of the rotation stop by extending through the first component in a direction that is substantially parallel to the rotation axis;
    detecting a rotational position of the first portion relative to the second portion; and
    adjusting an electronic display of images captured by the camera based on the detected rotational position.

2. The method of claim 1, wherein the first portion comprises a knob and the second portion comprises a handle, the knob being rotatable relative to the handle to rotate the camera relative to the handle.

3. The surgical method of claim 1, wherein the rotation stop limits rotation of the first component relative to the second component about the rotation axis to a range greater than 360 degrees and less than or equal to about 720 degrees.

4. The surgical method of claim 1, wherein, when the second component is rotated relative to the first component, a nut travels along a shaft between first and second rotation components to limit rotation of the first component relative to the second component about the rotation axis.

5. The surgical method of claim 1, wherein the retention feature comprises one or more spring tabs configured to maintain the axial position of the first component relative to the second component.

6. The surgical method of claim 1, wherein the electronic display of images is adjusted by rotating the first portion of the instrument relative to the second portion of the instrument in accordance with the detected rotation.

7. The surgical method of claim 1, wherein the instrument further comprises an optical fiber.

8. The surgical method of claim 7, further comprising directing light with the optical fiber from a light source proximal to the second portion of the instrument to a location adjacent the distal end of the instrument.

* * * * *